US010722542B2

(12) United States Patent
Martinsen et al.

(10) Patent No.: US 10,722,542 B2
(45) Date of Patent: Jul. 28, 2020

(54) NON-WINTERIZED, STANDARDIZED MARINE SOURCE OIL PRODUCTS AND METHODS OF MAKING THEREOF

(71) Applicant: Ambo Innovations, LLC, Osprey, FL (US)

(72) Inventors: Bo Reidar Martinsen, Osprey, FL (US); Leif Andreas Riege, Gressvik (NO)

(73) Assignee: AMBO INNOVATIONS, LLC, Osprey, FL (US)

( * ) Notice: Subject to any disclaimer, the term of this patent is extended or adjusted under 35 U.S.C. 154(b) by 0 days.

(21) Appl. No.: 15/619,691

(22) Filed: Jun. 12, 2017

(65) Prior Publication Data

US 2017/0360846 A1 Dec. 21, 2017

Related U.S. Application Data

(60) Provisional application No. 62/350,785, filed on Jun. 16, 2016.

(51) Int. Cl.
*A61K 35/60* (2006.01)
*A61K 31/4045* (2006.01)
(Continued)

(52) U.S. Cl.
CPC ............ *A61K 35/60* (2013.01); *A23L 33/115* (2016.08); *A23L 33/12* (2016.08); *A23L 33/155* (2016.08);
(Continued)

(58) Field of Classification Search
None
See application file for complete search history.

(56) References Cited

U.S. PATENT DOCUMENTS 2,796,188 A * 6/1957 Kurkjian ................. A61J 9/008
215/11.1
6,518,049 B1 * 2/2003 Haraldsson ............... C11C 3/02
435/134
(Continued)

FOREIGN PATENT DOCUMENTS

WO 2009029793 A1 3/2009
WO WO-2010149815 A1 * 12/2010 ............... A23D 9/00
(Continued)

OTHER PUBLICATIONS

English language translation of WO 2010/149815 A1 (Year: 2010).*
European Search Report for EP17176257 dated Oct. 16, 2017 (7 pages).

*Primary Examiner* — Dominic Lazaro
(74) *Attorney, Agent, or Firm* — Shumaker, Loop & Kendrick, LLP (57) ABSTRACT

Disclosed is a liquid medicament/supplement composition including a non-winterized marine source oil (e.g., oil derived from fish, krill, and/or squid), a food grade or pharmaceutically acceptable form of vitamin $D_3$ or a derivative thereof admixed in the non-winterized marine source oil, a food grade or pharmaceutically acceptable form of vitamin A or a derivative thereof admixed in the non-winterized marine source oil, optionally a food grade or pharmaceutically acceptable form of CoQ10 or a derivative thereof admixed in the non-winterized marine source oil, a food grade or pharmaceutically acceptable form of concentrated eicosapentaenoic acid and docosahexaenoic acid or ethyl ester, glyceride ester or salt of the acid and polyphenol rich vegetable oil admixed in the non-winterized marine source oil, and optionally a food grade or pharmaceutically acceptable form of melatonin or a derivative thereof admixed in the non-winterized marine source oil. The liquid medicament/supplement composition preferably has an oxi-
(Continued)

dation amount measured as totox of less than 5, and the liquid medicament/supplement composition preferably has an overall eicosapentaenoic acid to docosahexaenoic acid ratio (DHA:EPA) ranging from 2:1 to 1:2 at a concentration ranging from 15 to 35 wt % of total liquid weight calculated as weight % of the corresponding free acid.

12 Claims, 2 Drawing Sheets

(51) Int. Cl.
| | | |
|---|---|---|
| *A61K 31/202* | (2006.01) | |
| *A61K 31/122* | (2006.01) | |
| *A61K 31/07* | (2006.01) | |
| *A23L 33/12* | (2016.01) | |
| *A61J 1/14* | (2006.01) | |
| *A61K 9/00* | (2006.01) | |
| *A23L 33/155* | (2016.01) | |
| *A23L 33/00* | (2016.01) | |
| *A23P 10/30* | (2016.01) | |
| *A23L 33/115* | (2016.01) | |
| *A61K 31/593* | (2006.01) | |
| *A61K 9/48* | (2006.01) | |

(52) U.S. Cl.
CPC .............. *A23L 33/40* (2016.08); *A23P 10/30* (2016.08); *A61J 1/1418* (2015.05); *A61K 9/0053* (2013.01); *A61K 9/48* (2013.01); *A61K 31/07* (2013.01); *A61K 31/122* (2013.01); *A61K 31/202* (2013.01); *A61K 31/4045* (2013.01); *A61K 31/593* (2013.01); *A23V 2002/00* (2013.01)

(56) References Cited

U.S. PATENT DOCUMENTS

2009/0202679 A1\* 8/2009 Mathisen .................. A23L 2/02
426/61
2012/0156296 A1 6/2012 Omegatri
2012/0184760 A1\* 7/2012 Saebo ..................... C11C 3/003
554/224

FOREIGN PATENT DOCUMENTS

| WO | 2013150384 A1 | 10/2013 | |
| WO | 2015085045 A1 | 6/2015 | |
| WO | WO-2015085045 A1 \* | 6/2015 | ........... A61K 36/185 |

\* cited by examiner

NON-WINTERIZED, STANDARDIZED MARINE SOURCE OIL PRODUCTS AND METHODS OF MAKING THEREOF

TECHNICAL FIELD

The present invention relates generally to the field of marine source oils including fish oil(s), and more particularly, to non-winterized, standardized marine source oil product(s) having a totox of 5 or less and fixed EPA/DHA ratios.

BACKGROUND

Throughout history eating fish has been associated with good health, fertility, and helpful in alleviating many illnesses. In the late 1700s a clinic in Manchester, England discovered that cod liver oil miraculously "healed" chronic pain from arthritis and the news spread quickly across Europe and gave rise to the popularity of the oil.

In the 1970s, two Danish researchers theorized that the cardiac benefits of eating fish were linked to a fatty acid group called the Omega 3s, which make up approximately 10 to 30 wt % of extracted fish oil while the remainder of the oil is comprised of saturated, mono unsaturated, and other poly unsaturated parts. Among the Omega 3 fatty acids, two fatty acids (eicosapentaenoic acid (EPA) and docosahexaenoic acid (DHA)) were particularly prevalent and garnered great scientific and popular notoriety. However, researchers ignored the fact that, for example, cod liver oil not only contains EPA and DHA but also more than 10 other types of Omega 3 fatty acids. Moreover, many fish oils include endogenous vitamins such as Vitamins A, D, E, Cofactors such as CoQ10, and melatonin, but ratios and concentrations of these vitamins, cofactors, and melatonin vary dramatically across fish species.

Due to the positive effects associated with fish oils, many clinical trials have been conducted with various fish oils, DHA formulations, EPA formulations, and/or DHA/EPA formulations, but these trials generally ignore the fact that concentrations of fatty acids, vitamins, cofactors, and melatonin vary dramatically across fish species. Moreover, these trials further ignore how this variation affects a subject's epigenetic response (e.g., gene expression) when administered with these formulations. The ultimate consequence is that clinical trials only quantify EPA/DHA efficacy while concurrently failing to quantify efficacy of other active nutrients and freshness factor, which studies are beginning to show are also important for fish oil potency.

To further complicate matters in Omega 3 research and clinical medicine, different Omega 3 molecules have different physiological actions, and for the two main Omega 3 molecules (EPA and DHA), the science community is divided on their use and/or importance. One group advocates using EPA alone since EPA may be stronger anti inflammation substance than DHA while other groups advocate that DHA is most important since it is the longest molecule and the most likely to be lacking in one's diet. DHA is especially known for its nerve cell building abilities and crucial for mental functioning. It would therefore be advantageous to have an agreed upon EPA/DHA ratio that would be suitable to a multitude of medical conditions.

Other problems often associated with fish oils are the off-putting odor and taste (e.g., a "fishy" smell and/or taste), which acts as a deterrent for supplementing ones diet with these oils/supplements. These off-putting odors and tastes are attributed to oxidation of the unsaturated fatty acids as Omega-3 fatty acids and other chemical components in fish oils ("oxidized fish oils") during fish storage and the fish oil (i) rendering/purification, (ii) manufacture, and (iii) finished product storage processes. To make these oxidized fish oils more palatable, artificial flavoring(s) and taste masking agents are often added to further improve taste and increase the likelihood of consumption of these oxidized fish oils. In some instances, these oxidized fish oils are encapsulated within an encapsulating agent, including, for example, a thick gelatin coating/layer, which masks the fishy smells and tastes to increase ones desire to consume these oxidized fish oils. However, even though encapsulating fish oils may aid in masking the fishy smell, it should be further noted that fish oil oxidation continues to occur post-encapsulation—often increasing by more than 7.5 PoV and doubling in anisidine values (i.e., increased totox) within three weeks post-encapsulation. It should also be noted that these masking and encapsulating agents fail to completely obviate the "fishy" taste and smell, while also disadvantageously increasing production costs and manufacturing time for fish oil formulations.

Although masking agents and/or encapsulating agents are used as the current industry-wide solution to overcome the fishy smell and taste of these oxidized fish oils, a major underlying problem remains. Specifically, oxidized fish oils have decreased health benefits, decreased bioavailability, and increased toxicity attributed to (i) increased totox (i.e., totox >10) and (ii) decreased EPA and DHA concentrations (and ratios relative to each other) resulting from processing (i.e., extraction and purification) when compared to totox and EPA and DHA concentrations (and ratios relative to each other) in natural, endogenous fish oil in viable fish. It should be further noted that fish oil oxidation cannot be reversed. Thus, once fish oil becomes oxidized and/or rancid it remains oxidized thereby permanently having decreased health benefits and decreased bioavailability. Also, the products formed during the oxidation of oils (rancemates) are unsaturated aldehydes and ketones as well as other reactive unsaturated aliphatic hydrocarbons, known to be toxic.

In addition to the above mentioned problems, most, if not all, currently available fish oil(s)/fish oil supplements have been winterized (i.e., fractionated) thereby excluding some beneficial fatty acids initially present in these oils. Specifically, winterization is known in the art as the removal of glycerides (fat) with a melting point >0° C. from fish oil, thus potentially enhancing storability of these oils in low temperature environments. Winterization may occur by cooling the "neat fish oil" to approximately 0° C. thereby forming a liquid (oil)/crystal mixture and then separating the liquid portion ("olein") from the solid/crystalline portion ("stearin"). As the stearin portion contains many valuable chemical components including various fatty acids that act synergistically with the olein portion, winterized oils may have decreased bioavailability and decreased health benefits due to the removal of the stearin portion. In addition to decreased bioavailability of winterized fish oil, winterization of fish oils adds increased complexity, increased cost, and increased time period(s) for manufacture/production of fish oil formulations.

Another major problem plaguing currently marketed fish oils (i.e., both over the counter and prescription fish oil formulations) is the lack of standardization in these formulations. In other words, fish oil formulations vary greatly in, for example, fatty acid content (e.g., Omega-3 fatty acid content, as well as Omega-6, 7, 9, 11, and 13 fatty acid content), EPA and DHA concentrations (and ratios relative to each other), and totox thereby resulting in vastly different physiological and medical benefits obtained from these formulations. For example, many currently marketed formulations only include (i) concentrated EPA, (ii) concentrated DHA, and/or (iii) concentrated mixtures of EPA and DHA, but these formulations lack (or are highly deficient) in other important Omega-3 fatty acids such alpha-Linolenic acid (ALA), eicosadienoic acid (EDA), and docosapentaenoic acid (DPA), as well as Omega-6, 7, 9, 11 and 13 fatty acids that are typically found in natural fish oils but are removed when producing these concentrated EPA and/or DHA formulations. Unlike natural fish oils which have a neutral charge, these concentrated EPA formulations, concentrated DHA formulations, and/or concentrated mixtures of EPA and DHA have high in ethyl ester content resulting in increased polarity and thereby lowering the viscosity of the oil which may affect its physiological functioning. As another example, (i) Omega-3 content and (ii) EPA and DHA concentrations and ratios greatly vary in non-concentrated "natural" fish oils depending on the fish oil source (i.e., the type of fish used to produce the oil), time of the year the fish were obtained, the location from which the fish were obtained, and the refinement methods used to render/purify the fish oil. These factors also result in highly variable physiological and medical benefits. Furthermore, reduced viscosities of concentrated and/or winterized fish oils will also reduce its ability to be included in function foods or topical formulations like skin cream as the oil will more easily separate from solids and will also make added microencapsulated drugs included in fish oil medicinal formulations more noticeable and less palatable.

Another set of problems is connected to non-standardization of vitamin co factors in fish oil, e.g. Vitamin A and $D_3$. While the original and highly potent cod liver oil contains significant amounts of Vitamin A (up to 1000 IU/g) and $D_3$ (up to 100 IU/g) most fish oils on the market today have low levels of these nutrients because they are lost during the purification process and refining of the oil. Since many researchers believe that Vitamin A and $D_3$ are important co factors for proper Omega 3 function, some set/standardized values would be desirable.

Another important nutrient/hormone relevant to Omega 3 oil is the content of melatonin. This indole hormone is present in significant amounts in raw cod liver oil or tuna oil, but will typically be diminished during winterization and refining or in oil from fish in aqua culture where light is used to delay sex maturation (the light makes melatonin content in fish diminish). Since studies show that melatonin and Omega 3 exercise synergistic actions on a multiple of cell metabolic functions, it would be desirable to restore and/or supplement this amount but in many countries health authorities forbid adding melatonin to food.

As evidenced above, vast differences exist between the currently marketed fish oils, thus leading to vastly different physiological and medical benefits observed by users of these formulations. Thus, for at least the reasons, the above mentioned non-standardized fish oils, oxidized fish oils, winterized fish oils, and/or oxidized, winterized fish oils present multi-faceted problem(s) of decreased bioavailability, decreased health benefits, and/or highly unpredictable health benefits coupled with increased toxicity.

SUMMARY

Therefore, a need exists to provide compositions, along with methods of making these compositions that obviate the above mentioned industry-wide problems. Disclosed are standardized compositions formulated to minimize and/or eliminate the vast physiological and medical differences observed in the currently marketed over the counter and prescription marine source oil formulations (e.g., fish oil, krill oil, and/or squid oil) regardless of the original marine source. These standardized compositions can be used in clinical medicine and will not differ in essential content independent of whether the source is, for example, cod liver, herring, krill, and/or squid. The present invention is also important for environmental reasons because there aren't enough raw materials to cover the world's need of fish oil from a single marine source. Thus, the solution is to provide a standardized marine sourced oil (standardized composition) that can use most marine sources as raw materials and still maintain the most valuable active ingredients in the same concentrations and ratios that are found, for example, in fresh, non-modulated raw fish oil. It is preferred that these standardized oils can be precisely reproduced batch after batch, stable over time, and have qualities making it useful for Omega 3 supplementation, functional foods, skin cream applications or medical devices. As discussed in further detail below, these standardized formulations preferably include a non-winterized marine source oil having a low totox that are produced utilizing a process as disclosed in, for example, WO2015/085045 "Omega-3 Fatty Acid Articles Of Manufacture, And Methods And Apparatus For Making" to Martinsen et al., the disclosures of which are hereby incorporated by reference in their entirety. This non-winterized marine source oil is further supplemented with desired amounts of EPA concentrate, DHA concentrate, along with vegetable polyphenol rich oil like Flax seed oil or extra virgin olive oil (EVOO), lipophilic vitamins, and other desired chemical components (while maintaining low totox) to obtain a specified, standardized Omega-3 content and EPA/DHA concentration(s) and ratio(s) regardless of the marine source thereby resulting in a composition having consistent, predictable health benefits. In certain aspects, it is preferable to supplement the non-winterized marine source oil with EPA and/or DHA and polyphenol rich vegetable oil by adding a small amount of EPA concentrate, DHA concentrate, or mixtures thereof and small amounts of polyphenol rich vegetable oil to adjust EPA and DHA concentrations and ratios to a desired amount without disturbing the natural fatty acid balance in the non-winterized marine source oil. For example, in certain preferred aspects, if EPA and DHA concentration(s) are higher than desired at least one of flax seed oil, extra virgin olive oil, and/or a polyphenol rich vegetable oil may be added to dilute the overall concentration of EPA and/or DHA to obtain a standardized, desired EPA and/or DHA concentration in the liquid medicament(s)/supplement(s). These compositions are further preferably odorless, tasteless, or a combination thereof, thereby improving user/patient compliance by avoiding objections to the composition's taste.

Specifically disclosed are liquid medicament/supplement composition(s) including a non-winterized marine source oil, a pharmaceutically acceptable form of vitamin $D_3$ or derivative thereof admixed in the non-winterized marine source oil, a pharmaceutically acceptable form of vitamin A or a derivative thereof admixed in the non-winterized marine source oil, a food grade or pharmaceutically acceptable form of vegetable polyphenol rich oil admixed in the non-winterized marine source oil, optionally a pharmaceutically acceptable form of Coenzyme Q10 (CoQ10) or a derivative thereof admixed in the non-winterized marine source oil, concentrated eicosapentaenoic acid or, glyceride ester, ethyl ester or salt of the acid, concentrated docosahexaenoic acid, or glyceride ester, ethyl ester or salt of the acid or mixtures thereof admixed in the non-winterized marine source oil, and optionally a pharmaceutically acceptable form of melatonin or a derivative thereof admixed in the non-winterized marine source oil. The liquid medicament/supplement composition preferably has an oxidation amount (measured as totox) of 5 or less, and the liquid medicament/supplement composition preferably has an overall eicosapentaenoic acid to docosahexaenoic acid ratio (DHA:EPA) ranging from 2:1 to 1:2 in a concentration ranging from 15 to 35 wt %. As alluded to above, in certain preferred aspects, if EPA and DHA concentration(s) are higher than desired at least one of flax seed oil, extra virgin olive oil, and/or a polyphenol rich vegetable oil may be added to dilute the overall concentration of EPA and/or DHA to obtain a standardized, desired EPA and/or DHA concentration in the liquid medicament (s)/supplement(s). However, it is preferred to limit overall concentration of flax seed oil, extra virgin olive oil, and/or a polyphenol rich vegetable oil to a concentration of less than 25 wt % of total liquid weight, less than 20 wt % of total liquid weight, less than 15 wt % of total liquid weight, or less than 10 wt % of total liquid weight.

In certain aspects, the liquid medicament/supplement composition is tasteless, odorless, or a combination thereof.

In certain aspects, melatonin is present in the liquid medicament/supplement composition.

In certain aspects, the overall DHA:EPA ratio of the liquid medicament/supplement composition more preferably ranges from 1.5:1 to 1:1.5 and is most preferably 1:1. In certain aspects the overall DHA/EPA concentration of the liquid medicament/supplement composition more preferably ranges from 15 to 35 wt % of total liquid weight and is most preferably 25 wt % of total liquid weight.

In certain aspects, the liquid medicament/supplement composition is adapted for oral delivery, transdermal delivery, transmucosal delivery, or any combination thereof.

In certain aspects, the liquid medicament/supplement composition may be encapsulated in a capsule for gastrointestinal delivery.

In certain aspects, the non-winterized marine source oil is at least one comprising fish liver oil, cod liver oil, fish body oil, fish eye oil, fish meat oil, fish offal oil, oil from squid, oil from krill, or any combination thereof. In certain aspects, the non-winterized marine source oil is a fish oil including at least one of Norwegian Cod Liver Oil, Alaskan Cod Liver Oil, Peruvian fish body oil, South African fish body oil, Moroccan fish body oil, or any combination thereof. Examples of cod liver oil include liver oil from any of the Gadidae family, and may more specifically include liver oil from: *Gadus morhua* (Arctic cod, Atlantic cod), *Gadus microcephalus* (pacific cod), *Pollachius virens* (seith, pollock, pollack), *Pollachius pollochius* (lyr), *Melanogrammus aeglefinus* (hyse, haddock), or any combination thereof. Additional liver oil from sharks (e.g., Elasmobranchii) may also be used as the source of the non-winterized marine source oil. Fish oil and/or oil from additional marine sources used in the non-winterized marine source oil may further include oil from any one of the following: Scombridae (e.g., *Scombrus scombrus* (mackerel), *Thunnus* (tunafish class), *Engraulus ringens*, (anchoveta), *Sardinella* (e.g., *Sardinella longiceps*) (sardines), *Clupea* (*Clupea harengus*) (atlantic herring), *Mallotus* (e.g., *Mallotus villosus*) (lodde), Salmonidae (e.g., *Salmo salar, Salmo trutta trutta*) (Atlantic salmon and trout), *Todarodes sagittatus* (akkar, squid, callimari), Calanidae (e.g., *Calanus finmarchicus*), Euphausiacea (e.g., *Meganyctiphanes norvegica*) (krill), or any combination thereof.

Also disclosed are methods of producing the liquid medicament/supplement composition(s) including providing a non-winterized marine source oil having a totox of less than 5; admixing a pharmaceutically acceptable form of vitamin $D_3$ or a derivative thereof in the non-winterized marine source oil; admixing a pharmaceutically acceptable form of vitamin A or a derivative thereof in the non-winterized marine source oil; optionally admixing a pharmaceutically acceptable form of CoenzymeQ10 or a derivative thereof salt thereof in the non-winterized marine source oil; adjusting eicosapentaenoic acid or ethyl ester, glyceride ester or salt of the acid concentration in the non-winterized marine source oil, docosahexaenoic acid or ethyl ester, glyceride ester or salt of the acid concentration in the non-winterized marine source oil, or a combination thereof by admixing concentrated eicosapentaenoic acid, or ethyl ester, glyceride ester or salt of the acid, concentrated docosahexaenoic acid, or ethyl ester, glyceride ester or salt of the acid a combination thereof and polyphenol rich vegetable oil with the non-winterized marine source oil (having a concentration of less than 25 wt % of total liquid weight); and optionally admixing melatonin or a salt thereof in the non-winterized marine source oil thereby producing the liquid medicament/supplement composition, wherein: the liquid medicament/supplement composition has a totox of less than 5, and the liquid medicament/supplement composition has liquid medicament/supplement composition has an overall eicosapentaenoic acid to docosahexaenoic acid ratio (DHA:EPA) ranging from 2:1 to 1:2 and having a concentration of 15 to 35 wt % of the medicament/supplement. In certain aspects, the admixed concentrated eicosapentaenoic acid, or ethyl ester, glyceride ester or salt of the acid, concentrated docosahexaenoic acid, or ethyl ester, glyceride ester or salt of the acid a combination thereof is present at a concentration of less than 20 wt %, less than 15 wt %, less than 10 wt %, less than 5 wt %, or less than 2 wt % of the total liquid weight.

In certain aspects, preferred containers are used for storing the disclosed liquid medicament/supplement compositions that preferably limit and/or eliminate the composition's oxidation while stored therein. For example this container may include an internal chamber containing a liquid medicament/supplement composition, and a cap that threadly engages a top portion of the internal chamber to seal the internal chamber, the cap having an inverted nipple such that the internal nipple protrudes into the internal chamber when the cap threadly engages the top portion of the internal chamber thereby reducing and/or limiting air within the internal chamber thereby reducing and/or eliminating oxidation of the liquid medicament/supplement while stored in the container.

In certain aspects, the features of disclosed compositions (e.g., a standardized composition including a non-winterized marine source oil having a predetermined Omega-3 fatty acid content, a predetermined EPA and/or DHA content, and predetermined vitamin content) make the compositions ideal for medical multipurpose use in combination with foods, drugs, topical creams, and ointments because predictable physiological and medical benefits may be consistently obtained with these compositions.

Additional features, aspects and advantages of the invention will be set forth in the detailed description which follows, and in part will be readily apparent to those skilled in the art from that description or recognized by practicing the invention as described herein. It is to be understood that both the foregoing general description and the following detailed description present various embodiments of the invention, and are intended to provide an overview or framework for understanding the nature and character of the invention as it is claimed. The accompanying drawings are included to provide a further understanding of the invention, and are incorporated in and constitute a part of this specification.

BRIEF DESCRIPTION OF THE DRAWINGS

These and other features, aspects and advantages of the present invention are better understood when the following detailed description of the invention is read with reference to the accompanying drawings, in which.

DETAILED DESCRIPTION

The present invention will now be described more fully hereinafter. It is to be understood that the aspects described below are not limited to specific compounds, synthetic methods, or uses as such may, of course, vary. It is also to be understood that the terminology used herein is for the purpose of describing particular aspects only and is not intended to be limiting. However, the invention may be embodied in many different forms and should not be construed as limited to the representative embodiments set forth herein. The exemplary embodiments are provided so that this disclosure will be both thorough and complete, and will fully convey the scope of the invention and enable one of ordinary skill in the art to make, use and practice the invention.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise.

"Optional" or "optionally" means that the subsequently described event or circumstance can or cannot occur, and that the description includes instances where the event or circumstance occurs and instances where it does not. For example, the phrase "optionally melatonin" means that melatonin may or may not be present in the compositions and/or methods described herein.

As used herein, the term "about" is used to provide flexibility to a numerical range endpoint by providing that a given value may be "slightly above" or "slightly below" the endpoint without affecting the desired result.

"Non-winterized" as disclosed herein refers to a non-concentrated marine source oil containing both stearin and olein portions in which glycerides having a melting point >0° C. have not been removed from the marine source oil via separation methods (e.g., fractionation, centrifugation, chromatographic techniques), as well as a full spectrum of Omega-3 fatty acids and Omega-6, 7, 9, 11, and 13 fatty acids found in the marine oil source and being present in the marine source oil.

"Standardized" as disclosed herein refers to the supplementation of the non-winterized marine source oil obtained after extracting the oil from the desired marine source (e.g., Norwegian cod, Alaskan cod, Peruvian fish body, South African fish body, Moroccan fish body, krill, squid) with, for example, DHA and/or EPA concentrate and Omega 3 fatty acids to obtain a desired concentration in the non-winterized, standardized marine source oil. Standardization further means that the contemplated composition(s) can be precisely reproduced batch after batch over time and with acceptable chemical stability under optimal storage conditions.

"Totox" is a well-established scientific notation for the oxidation level of an oil product containing unsaturated fatty acid moieties and readily understood by those skilled in the art. A "low oxidation" as set forth by the Global Organization for EPA and DHA Omega 3s "GOED" (http://goedOmega3.com/) is a totox of less than 10. PoV is measured as milliequivalents hydroperoxide(s) per kilogram of oil. PoV is increasingly seen with millimoles per kg of oil as unit. This unit gives half the numeric value of the milliequivalent calculation. TOTOX would then be 4×PoV+ AiV. AiV is a number without units (it is the blue light absorption of compounds formed by reaction between an aldehyde (or ketone) and anisidine. The procedure is an official American Oilchemists Society "AOCS" procedure (method).

"Marine source oil(s)" as disclosed herein refers to oil(s) extracted from a desired marine source including fish, krill, and/or squid) using a rendering and/or purification method that minimizes oxidation thereby resulting in totox <5. Preferably the marine source oil is rendered/purified through the method(s) disclosed in WO2015/085045 "Omega-3 Fatty Acid Articles Of Manufacture, And Methods And Apparatus For Making" to Martinsen et al. Exemplary marine sources for providing/rendering the marine source oil(s) include: fish liver oil from any of the Gadidae family, and may more specifically include liver oil from: *Gadus morhua* (Arctic cod, Atlantic cod), *Gadus microcephalus* (pacific cod), *Pollachius virens* (seith, pollock, pollack), *Pollachius pollochius* (lyr), *Melanogrammus aeglefinus* (hyse, haddock), or any combination thereof. Additional liver oil from sharks (e.g., Elasmobranchii) may also be used in the non-winterized marine source oil. Fish oil and/or oil from additional marine sources used in the non-winterized marine: source oil may further include oil from any one of the following: Scombridae (*Scombrus scombrus* (mackerel), *Thunnus* (tunafish class), Clupeidae (e.g., *Engraulus ringens*) (anchoveta), *Sardinella* (e.g., *Sardinella longicheps*) (sardines), *Clupea* (*Clupea harengus*) (atlantic herring), *Mallotus* (e.g., *Mallotus villosus*) (lodde), Salmonidae (e.g., *Salmo salar, Salmo trutta trutta*) (Atlantic salmon and trout), *Todarodes sagittatus* (akkar, squid, callimari), Calanidae (e.g., *Calanus finmarchicus*), Euphausiacea (e.g., *Meganyctiphanes norvegica*) (krill), or any combination thereof.

"Non-winterized standardized marine source oil" means a marine source oil as defined above that has not been subjected to winterization and that has been (i) supplemented with a DHA and/or EPA concentrate and vegetable polyphenol rich oil to obtain desired DHA/EPA concentration(s) and ratio(s), (ii) supplemented with the vitamin(s), optional cofactors, optional melatonin, and optional additive(s) described herein, and (iii) further has a specifically desired Omega-3 fatty acid concentration while having and/or maintaining a totox of less than 10 and most preferably 5 or less during production and storage (i.e., until consumed by a patient and/or user). The phrase "liquid medicament(s)/supplement(s)" is used interchangeably with the phrase "non-winterized standardized marine source oil" throughout this disclosure.

"Food grade" means FDA approved use for human or animal nutrition.

"Pharmaceutical grade" means FDA approved for medicinal use.

"Admixed" means to mix with or mixed together such that components are dispersed in the composition. If the composition is liquid, these components are sufficiently mixed such that the components do not precipitate out of solution, and in certain aspects, these components are homogeneously mixed/admixed and/or dispersed in the liquid medicament(s)/supplement(s).

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within the ranges as if each numerical value and sub-range is explicitly recited. As an illustration, a numerical range of "about 1 to 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc. as well as 1, 2, 3, 4, and 5, individually. The same principle applies to ranges reciting only one numerical value as a minimum or a maximum. Furthermore, such an interpretation should apply regardless of the breadth of the range or the characteristics being described.

The compositions and methods described herein can comprise, consist of, or consist essentially of the essential elements and limitations described herein, as well as any additional or optional ingredients, components, or limitations described herein or otherwise useful in nutritional formula applications.

It is understood that any given particular aspect of the disclosed compositions and methods can be easily compared to the specific examples and embodiments disclosed herein. By performing such a comparison, the relative efficacy of each particular embodiment can be easily determined. Particularly preferred compositions and methods are disclosed in the Examples herein, and it is understood that these compositions and methods, while not necessarily limiting, can be performed with any of the compositions and methods disclosed herein.

In certain aspects, disclosed are liquid medicament/supplement composition(s) that include a non-winterized marine source oil, a food grade or pharmaceutically acceptable form of vitamin $D_3$ or a derivative thereof admixed in the non-winterized marine source oil, a food grade or pharmaceutically acceptable form of vitamin A or a derivative thereof admixed in the non-winterized marine source oil, a food grade or pharmaceutically acceptable form of CoQ10 or a derivative thereof admixed in the non-winterized marine source oil, a food grade or pharmaceutically acceptable form of concentrated eicosapentaenoic acid and/or docosahexaenoic acid admixed in the non-winterized marine source oil, a food grade or pharmaceutically acceptable form of vegetable polyphenol rich oil admixed in the non-winterized marine source oil, and optionally a food grade or pharmaceutically acceptable form of melatonin or a derivative thereof admixed in the non-winterized marine source oil. The liquid medicament/supplement composition preferably has an oxidation amount (measured as totox) of 5 or less, and the liquid medicament/supplement composition preferably has an overall eicosapentaenoic acid to docosahexaenoic acid ratio (DHA:EPA) ranging from 2:1 to 1:2 in a concentration ranging from 15 to 35 wt % of total liquid weight. The liquid medicament/supplement composition(s) is preferably odorless and tasteless—not having a fishy taste or smell. In certain preferred aspects, this liquid medicament/supplement composition most preferably has a DHA:EPA ratio of 1:1 at a concentration of 25 wt % of total liquid weight. The below disclosures provide further detail regarding the individual components of the liquid medicament(s)/supplement(s).

Non-Winterized Marine Source Oil

As discussed above, the liquid medicaments/supplements disclosed herein include non-winterized marine source oil derived preferably from, for example, fish, krill, and/or squid. Examples may include Norwegian Cod, Norwegian Cod Liver, Alaskan Cod, Alaskan Cod Liver, Peruvian fish body, South African fish body, Moroccan fish body, or any combination thereof. Exemplary fish liver oils may be from any fish in the Gadidae family, and may more specifically include liver oil from: *Gadus morhua* (Arctic cod, Atlantic cod), *Gadus microcephalus* (pacific cod), *Pollachius virens* (seith, pollock, pollack), *Pollachius pollochius* (lyr), *Melanogrammus aeglefinus* (hyse, haddock), or any combination thereof. Additional liver oil from sharks (e.g., Elasmobranchii) may also be used in the non-winterized marine source oil. Fish oil and/or oil from additional marine sources used in the non-winterized marine source oil may further include oil from any one of the following: Scombridae (e.g., *Scombrus scombrus* (mackerel), *Thunnus* (tunafish class), Clupeidae (e.g., *Engraulus ringens*)(anchoveta), *Sardinella* (e.g., *Sardinella longiceps*) (sardines), *Clupea* (*Clupea harengus*) (atlantic herring), *Mallotus* (e.g., *Mallotus villosus*) (lodde), Salmonidae (e.g., *Salmo salar, Salmo trutta trutta*) (Atlantic salmon and trout), *Todarodes sagittatus* (akkar, squid, callimari) Calanidae (e.g., *Calanus finmarchicus*) Euphausiacea (e.g., *Meganyctiphanes norvegica*) (krill), or any combination thereof. A non-winterized marine source oil is preferred because this oil includes a complete fatty acid profile of both the above mentioned olein and stearin portions as well as Omega-6, 7, 9, 11, and 13 fatty acids that synergistically act to provide optimal health benefits including, but not limited to, reducing endogenous, cellular inflammation, reducing the risk of heart disease, increasing fertility, having positive effects on fetal development in utero, regulating fat metabolism, and aiding visual acuity. The non-winterized marine source oil may be preferably obtained by using extraction/purification processes as disclosed in WO2015/085045 "Omega-3 Fatty Acid Articles Of Manufacture, And Methods And Apparatus For Making" to Martinsen et al., the disclosures of which are hereby incorporated by reference in their entirety. During these processes, antioxidants and melatonin are preferably added to limit oxidation (e.g., maintaining a totox of less than 10 and preferably 5 or less) while rendering/purifying the non-winterized marine source oil.

By limiting non-winterized marine source oil oxidation during processing, improved physiological effects may be achieved while concurrently avoiding marine source oil rancidity and toxicity. For example, in certain preferred aspects, the non-winterized oil maintains a totox of less than 10, more preferably less than 7.5, and most preferably 5 or less throughout extraction/purification and in the liquid medicament(s)/supplement(s). In certain aspects, the non-winterized marine source oil maintains a totox range from 2.5 to 10, from 2.5 to 7.5, from 3 to 8, from 3 to 6, from 4 to 8, from 4 to 6, from 4 to 5.5 throughout (i) extraction/purification and (ii) in the disclosed liquid medicament(s)/supplement(s).

To further obtain desired bioavailability and beneficial health effects, it is desired that the non-winterized marine source oil have specified concentrations/amounts of Omega-3 fatty acids to obtain a desired, standardized Omega-3 fatty acid concentration in the liquid medicament(s)/supplement(s). In the non-winterized marine source oil, overall Omega-3 fatty acid concentration is from 15 to 35 wt/wt %, from 22 to 35 wt/wt %, from 24 to 30 wt/wt %, or from 24 to 28 wt/wt %. In certain aspects, the overall Omega-3 fatty acid concentration in the liquid medicament(s)/supplement(s) ranges from 20 to 30 wt/wt %, from 22 to 38 wt/wt %, or from 24 to 26 wt/wt %. In certain preferred aspects, overall Omega-3 fatty acid concentration in the liquid medicament(s)/supplement(s) is about 24 wt/wt %, about 25 wt/wt %, about 26 wt/wt %, or about 27 wt/wt %.

DHA and EPA Concentration(s) and Ratio(s)

To further enhance bioavailability and beneficial health effects of the liquid medicament(s)/supplement(s), it is also preferable to supplement the non-winterized marine source oil with food grade and/or pharmaceutical grade EPA and/or DHA by adding a small amount of EPA concentrate, DHA concentrate, or mixtures thereof to adjust EPA and DHA ratios to a desired amount without disturbing the natural fatty acid balance in the non-winterized marine source oil, thereby obtaining a desired, standardized EPA/DHA ratio(s) and then to admix polyphenol rich vegetable oil like flax seed oil to obtain the desired EPA/DHA oil concentration in the final liquid medicament/supplement regardless of the source of the marine oil. The standardization of EPA/DHA concentration(s) and ratio(s) further ensures that consistent physiological and medical benefits are achieved when using the liquid medicament(s)/supplement(s) regardless of the source of the marine oil. When supplementing the non-winterized marine source oil with the DHA and/or EPA concentrate(s) and vegetable oil, it is further required to maintain a totox of less than 10, more preferably less than 7.5, and most preferably 5 or less. In certain aspects, the non-winterized marine source oil maintains a totox range from 2.5 to 10, from 2.5 to 7.5, from 3 to 8, from 3 to 6, from 4 to 8, from 4 to 6, from 4 to 5.5 during supplementation with the DHA and/or EPA concentrate(s) and polyphenol rich vegetable oil.

In certain aspects, it is desired that the liquid medicament(s)/supplement(s) have an overall DHA:EPA ratio ranging from 2:1 to 1:2, more preferably 1.5:1 to 1:1.5, even more preferably 1.25:1 to 1:1.25, and most preferably 1:1, wherein DHA and/or EPA concentrations in the non-winterized marine source oil were adjusted to have these ratios by adding small amounts of EPA and/or DHA concentrates to the non-winterized marine source oil. In certain aspects, overall DHA concentration in the liquid medicament(s)/supplement(s) ranges from 8 to 20 wt %, 10 to 17 wt %, or 12 to 16 wt %. In certain aspects, overall EPA concentration in the liquid medicament(s)/supplement(s) ranges from 8 to 20 wt %, 10 to 17 wt %, or 12 to 16 wt %. When present in the medicament(s)/supplement(s), concentrated eicosapentaenoic acid or ethyl ester, glyceride ester or salt of the acid, concentrated docosahexaenoic acid or ethyl ester, glyceride ester or salt of the acid, or mixtures thereof admixed in the non-winterized marine source oil are present at a concentration of less than 20 wt % of total liquid weight, at a concentration of less than 15 wt % of total liquid weight, at a concentration of less than 10 wt % of total liquid weight, at a concentration of less than 5 wt % of total liquid weight, or at a concentration of less than 2 wt % of total liquid weight. In certain aspects, DHA and EPA are present in the medicament(s)/supplement(s) at an overall concentration ranging from 15 to 35 wt % of total liquid weight, from 20 to 30 wt % of total liquid weight, or from 22 to 27 wt % of total liquid weight. In certain aspects, it is desired that the liquid medicament(s)/supplement(s) have an overall DHA:EPA ratio ranging from 2:1 to 1:2, more preferably 1.5:1 to 1:1.5, even more preferably 1.25:1 to 1:1.25, and most preferably 1:1 at an overall concentration ranging from 15 to 35 wt % of total liquid weight, from 20 to 30 wt % of total liquid weight, or from 22 to 27 wt % of total liquid weight. In certain preferred aspects, the overall DHA:EPA ratio is 1:1 having an overall DHA and EPA concentration of 25 wt % of total liquid weight.

Vitamin(s)

To further enhance bioavailability and beneficial health effects of the liquid medicament(s)/supplement(s), lipophilic vitamins are additionally admixed with the non-winterized marine source oil along with the DHA/EPA concentrate. Examples of lipophilic vitamins include a food grade or pharmaceutically acceptable form of Vitamin A (retinol/beta carotene) or a derivative thereof, a food grade or pharmaceutically acceptable form of Vitamin D (e.g., Vitamin $D_2$ and/or $D_3$) or a derivative thereof, a food grade or pharmaceutically acceptable form of Vitamin E (tocopherols or trinutriols) or a derivative thereof, and a food grade or pharmaceutically acceptable form of Vitamin $K_1$ and/or $K_2$ or a derivative thereof. In certain aspects, Vitamin C in, for example, oil soluble form may also be included in the liquid medicament(s)/supplement(s). In addition to the enhanced bioavailability of the liquid medicament(s)/supplement(s), the lipophilic vitamin(s) concurrently and advantageously act to sequester oxygen radicals (e.g., free radicals), thereby reducing and/or preventing oxidation in these liquid medicament(s)/supplements. Specifically, when admixing the vitamin(s), it is preferred that this mixture maintains a totox of less than 10, more preferably less than 7.5, and most preferably 5 or less.

The liquid medicament(s)/supplement(s) may specifically include a food grade or pharmaceutically acceptable form of Vitamin A or a derivative thereof, a food grade or pharmaceutically acceptable form of Vitamin D (e.g., Vitamin $D_2$ and/or $D_3$) or a derivative thereof, a food grade or pharmaceutically acceptable form of Vitamin E or a derivative thereof, a food grade or pharmaceutically acceptable form of Vitamin K or a derivative thereof, or any combination thereof. Each of these lipophilic vitamins may be independently present in the liquid medicament/supplement at concentrations ranging from, for example, 20 to 500 IU/ml oil and/or from 15 to 500 mg/g oil. In certain aspects, at least a food grade or pharmaceutically acceptable form of Vitamin A or a derivative thereof and a food grade or pharmaceutically acceptable form of Vitamin $D_3$ or a derivative thereof are included in the liquid medicament(s)/supplement(s) because of physiologically synergistic effects with the non-winterized oil and their antioxidant abilities The concentration of Vitamin A or the derivative thereof in the liquid medicament(s)/supplement(s) ranges from 50 to 200 IU/ml oil, from 75 to 150 IU/ml oil, from 100 to 125 IU/ml oil. The concentration of Vitamin $D_3$ or the derivative thereof in the liquid medicament(s)/supplement(s) ranges from 25 to 200 IU/ml oil, from 50 to 175 IU/ml oil, 75 to 150 IU/ml oil, or from 100 to 125 IU/ml oil. The concentration of Vitamin E or the derivative thereof in the liquid medicament(s)/supplement(s) ranges from 15 to 100 mg/g oil, from 25 to 90 mg/g oil, from 45 to 75 mg/g oil, or from 60 to 70 mg/g oil.

Cofactors

To also further enhance bioavailability and beneficial health effects of the liquid medicament(s)/supplement(s), one or more cofactors may be optionally admixed in the non-winterized marine source oil along with the above mentioned DHA and/or EPA concentrate, vegetable polyphenol rich oil and vitamins while maintaining a totox of less than 10, more preferably less than 7.5, and most preferably 5 or less. In certain aspects, these cofactors are non-vitamin cofactors including, but not limited to, a food grade or pharmaceutically acceptable form of Coenzyme Q (Coenzyme Q10) or a derivative thereof, a food grade or pharmaceutically acceptable form of Coenzyme B or a derivative thereof, a food grade or pharmaceutically acceptable form of Coenzyme M or a derivative thereof, adenosine triphosphate (ATP or a salt thereof), or any combination thereof.

The above mentioned non-vitamin cofactors may each be independently present in the liquid medicament(s)/supplement(s) at a concentration ranging from 0.3 to 10 mg/ml oil. Of particular interest and importance among these cofactors is the food grade or pharmaceutically acceptable form of Coenzyme Q10 or a derivative thereof. Without wishing to be bound by theory, Coenzyme Q10 is thought to work in synergy with Omega 3 fatty acids and melatonin in the cellular/mitochondria energy chaises. Thus, in certain preferred aspects, Coenzyme Q10 or a derivative thereof is admixed/supplemented into the non-winterized marine source oil along with the above mentioned DHA and/or EPA concentrate(s), vegetable oil and vitamins at a concentration ranging from 0.3 to 10 mg/ml oil, from 1 to 7 mg/ml oil, from 2 to 5 mg/ml oil to further supplement Coenzyme Q10 concentrations naturally occurring in the marine source oil thereby potentially ensuring optimal bioavailability and beneficial health effects of the liquid medicament(s)/supplement(s).

Melatonin

A food grade or pharmaceutically acceptable form of melatonin or derivative thereof may also be optionally admixed to the non-winterized marine source oil having the above mentioned non-winterized marine source oil, the DHA and/or EPA concentrate, vitamin(s), and cofactor(s) while maintaining a totox of less than 10, more preferably less than 7.5, and most preferably 5 or less when preparing the liquid medicament(s)/supplement(s). Melatonin is an important hormone that regulates circadian rhythm in animals, thus helping maintain a proper sleep/wake cycle in addition to being a very effective anti-oxidant/free radical scavenger. Melatonin has also been implicated blood pressure regulation, immunomodulation (e.g., regulating inflammation), and reducing symptoms associated with many autoimmune disorders. It should be further noted that few scientifically proven adverse side effects have ever been documented from melatonin supplementation. The chemical structure of melatonin is shown below as Formula I.

FORMULA I

Moreover, melatonin has antioxidant properties, which are desirable in order to maintain low totox (i.e., of less than 10, more preferably less than 7.5, and most preferably 5 or less) of the liquid medicament(s)/supplement(s). An important characteristic of melatonin that distinguishes it from other classic radical scavengers/antioxidants is that its metabolites are also scavengers in what is referred to as a cascade reaction. Thus, even if melatonin is degraded/breaks down, its metabolites may still function as antioxidants to sequester free radicals, thus preventing oxidation of, for example, the liquid medicament(s)/supplement(s) disclosed herein. Without wishing to be bound by theory, melatonin is also thought to synergistically interact with other antioxidants, for example, lipophilic vitamins such as Vitamin A, Vitamin D (e.g., Vitamin $D_3$), and/or Vitamin E to enhance overall antioxidant properties and effectiveness. Melatonin has been proven to be twice as active as vitamin E, which is believed to be the most effective lipophilic vitamin antioxidant. Also different from many other antioxidants, such as vitamin E, melatonin has amphiphilic properties, which may further allow this compound to interact with both lipophilic and hydrophilic portions of cells and/or tissues in animals. Thus, melatonin clearly displays the above mentioned positive benefits and may be included in the disclosed liquid medicament(s)/supplement(s) for at least these reasons. Depending on the desired affect (e.g., antioxidant, antiinflammation/anti-inflammatory, etc.) in the medicament(s)/supplement(s), melatonin may be added to the disclosed liquid medicament(s)/supplement(s) at various concentrations. When included in the disclosed liquid medicament(s)/supplement(s), melatonin or the salt thereof is present at a concentration of up to 100 mg, up to 75 mg, up to 50 mg, up to 25 mg, up to 10 mg, up to 5 mg, or up to 3 mg. For example, when included in the disclosed liquid medicament(s)/supplement(s), melatonin or the salt thereof is present at a concentration of from 0.1 mg to 100 mg, from 0.1 mg to 75 mg, from 0.1 mg to 50 mg, from 0.1 mg to 25 mg, from 0.1 mg to 10 mg, from 0.1 mg to 5 mg, from 3 mg to 100 mg, from 3 mg to 75 mg, from 3 mg to 50 mg, from 3 mg to 25 mg, from 3 mg to 10 mg, from 10 mg to 100 mg, from 10 mg to 75 mg, from 10 mg to 50 mg, from 10 mg to 25 mg, from 25 mg to 100 mg, from 25 mg to 75 mg, from 25 mg to 50 mg, from 25 mg to 35 mg, from 40 mg to 100 mg, from 40 mg to 75 mg, from 40 mg to 50 mg, from 65 mg to 100 mg, from 65 mg to 85 mg, from 65 mg to 75 mg, from 65 mg to 70 mg, from 80 mg to 100 mg, from 80 mg to 95 mg, from 80 mg to 90 mg, from 80 mg to 85 mg, from 85 mg to 100 mg, from 85 mg to 95 mg, from 85 mg to 90 mg, from 90 mg to 100 mg, from 90 mg to 95 mg, or from 95 mg to 100 mg. In lower concentrations of melatonin are desired, melatonin may be present in the liquid medicament(s)/supplement(s) at a concentration ranging from 0.1 mg to 3 mg, from 0.15 mg to 2.5 mg, from 0.15 to 2.0 mg, from 0.175 mg to 2.0 mg, from 0.175 mg to 1.75 mg, from 0.175 mg to 1.5 mg, from 0.2 mg to 1.5 mg, from 0.2 mg to 1.75 mg, from 0.2 mg to 1.5 mg, from 0.2 mg to 1.25 mg, or from 0.2 mg to 1.0 mg.

Optional Additives

In addition to the above mentioned components, the liquid medicament(s)/supplements disclosed herein may further include optional additives. For example and although the disclosed liquid medicament(s)/supplement(s) are essentially odorless and tasteless due to low totox, natural or artificial flavorings may be added to the liquid medicament(s)/supplement(s) to provide a desired taste to these medicament(s)/supplement(s). Natural or artificial flavorings may include fruit punch, orange, lemon, or any known flavorings at sufficient concentration(s) to provide the medicament/supplement with the desired taste. One skilled in the art would readily understand how to admix these flavorings to the medicament(s)/supplement(s) to provide the desired taste. Likewise, one skilled in the art would readily understand how to provide natural or artificial fragrance(s) to these medicament(s)/supplement(s) if an odor/smell is desired.

Other additives may include, for example, lutein, astaxanthin, resveratrol, fatty alcohols (waxes), beta glucan, lecithin, phospholipids (e.g., phosphatidylcholine, phosphatidylserine, phosphatidylinositol), green tea or extracts thereof, or any combination thereof.

Delivery Forms

Any combination of food grade and pharmaceutical grade compositions of any of the above non-winterized marine source oil(s), DHA and/or EPA concentrate(s), polyphenol rich vegetable oil, vitamin(s) or salts thereof, cofactors or salts thereof, melatonin or salts thereof, and optional additives may be used when formulating the liquid medicament(s)/supplement(s), and these liquid medicament(s)/supplement(s) can be formulated in any excipient the biological system or entity can tolerate. Non-aqueous vehicles, such as fixed oils, vegetable oils such as olive oil, flax seed oil and sesame oil, propylene glycol, and polyethylene glycol can also be used to further enhance delivery and efficacy of the liquid medicament(s)/supplement(s). Other useful formulations include suspensions containing viscosity enhancing agents, such as sodium carboxymethylcellulose, sorbitol, dextran, xanthan, lecithin, beta glucan, hyaluronic acid, glycerin. Excipients can also contain minor amounts of additives, such as substances that enhance isotonicity and chemical stability. Examples of buffers include phosphate buffer, bicarbonate buffer and Tris buffer, while examples of preservatives include thimerosol, cresols, formalin and benzyl alcohol and phenoxyethanol.

Food grade and pharmaceutical grade carriers are known to those skilled in the art. These most typically would be standard carriers for administration to humans and animals, including solutions such as buffered solutions at physiological pH.

Food grade and pharmaceutical grade compositions can include carriers, thickeners, diluents, buffers, preservatives, surface active agents and the like in addition to the molecule of choice.

The disclosed liquid medicament(s)/supplement(s) compositions can be administered in a number of ways depending on whether local or systemic treatment is desired, and on the area to be treated. Administration can be orally, sublingually, transdermally, and/or transmucosally.

Formulations for administration can include ointments, lotions, creams, gels, drops, sprays, liquids and capsules. Because the liquid medicaments/supplements disclosed herein have higher viscosity than other currently marketed fish, krill, and/or squid oils, the disclosed liquid medicaments/supplements can be used by itself as food supplement, in cosmetic or topical creams or ointments, suppositories, vaginal applications, eye drops, mouth wash, and will be more stable as ingredient in functional foods like fortified cookies, chocolates, salad dressings, fruit juices and smoothies with lower risk of water/oil separation.

Dosing is dependent on severity and responsiveness of the condition to be treated, but will normally be one or more doses per day, with course of treatment lasting from several days to several months or until one of ordinary skill in the art determines the delivery should cease. Persons of ordinary skill can easily determine optimum dosages, dosing methodologies and repetition rates. For example, the disclosed liquid medicament(s)/supplement(s) may be provided sublingually to prevent and/or treat, for example, periodontitis (i.e., preventing and/or reducing buccal inflammation especially related to the gum line inflammation). The medicament(s)/supplement(s) disclosed herein may be useful in eye lotions or drops to prevent and/or or treat dry eye syndrome, cataracts, burns, bed sores, chronic wounds, eczema, psoriasis, vaginitis, various dermatoses, post-surgery scarring (e.g., keloid scarring), skin cancers, sun burn and skin damage associated with sun burns, and/or may be used as a prophylactic skin treatment due to its anti-aging skin effects. It is understood that any given particular aspect of the disclosed compositions and methods can be easily compared to the specific examples and embodiments disclosed herein based reagents discussed in the Examples. By performing such a comparison, the relative efficacy of each particular embodiment can be easily determined. Particularly preferred compositions and methods are disclosed in the Examples herein, and it is understood that these compositions and methods, while not necessarily limiting, can be performed with any of the compositions and methods disclosed herein.

Packaging of Liquid Medicament/Supplement Composition(s)

Figure 1A:
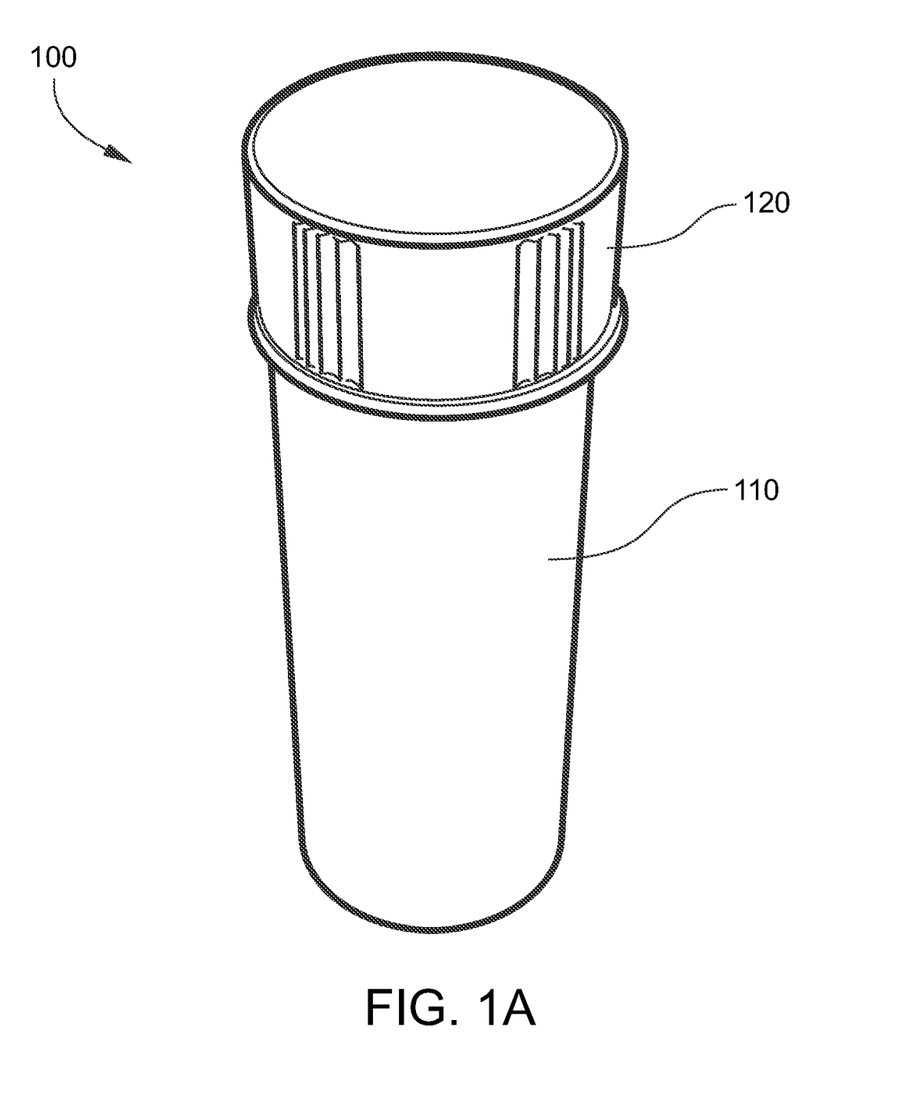
FIGS. 1A and 1B depict a sealable container adapted to reduce oxidation of the non-winterized, standardized marine source oil product while stored therein.
Figure 1B:
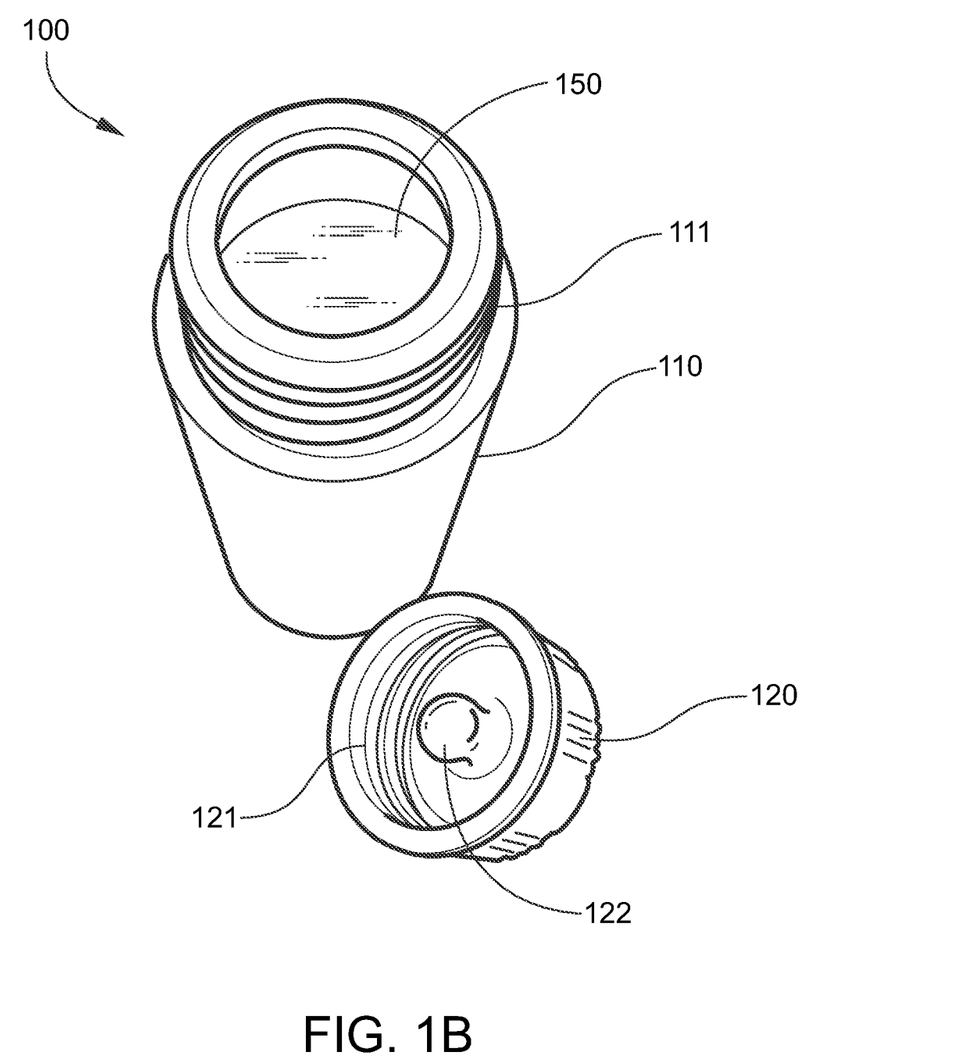

In certain embodiments, the liquid medicament(s)/supplement(s) may be packaged and/or stored in specialized containers that further limit oxidation. As shown in FIGS. 1A and 1B, a container 100 including an internal chamber 110 containing the disclosed liquid medicament/supplement composition(s) 150 is disclosed. Container 100 further includes cap 120 having an inner diameter portion 121 adapted to threadly engage a top, outer diameter portion 111 of internal chamber 110 to seal the internal chamber along with the contents stored/housed therein (i.e., the disclosed liquid medicament(s)/supplement(s)). Cap 120 has an inverted nipple 122 that protrudes into the internal chamber when the cap threadly engages the top portion of the internal chamber thereby forcing air (i.e., oxygen and other gases) out of the internal chamber, which further limits/reduces oxidation of the disclosed medicament(s)/supplement(s) stored therein.

In certain aspects, the internal chamber 110 is formed of glass (and/or an oxygen barrier film) and cap 120 is formed of a thermoplastic resin (and/or an oxygen barrier film), each being having minimal electron donors and receptors on its surface thereby further limiting the occurrence of redox reactions between the container 100 and liquid medicament(s)/supplement(s) 150 stored/housed therein. This beneficially minimizes oxidation of the liquid medicament(s)/supplement(s) until a user opens cap 120 to use the liquid medicament(s)/supplement(s). If glass is used as the internal chamber, this glass may further be surface treated to further minimize the occurrence of redox reactions between the container 100 and liquid medicament(s)/supplement(s) 150.

In certain aspects, a single dose of the disclosed liquid medicament/supplement composition is included in the container 100. Container 100 volume capacity can vary, but in certain aspects, container 100 can store 1 mL to 20 mL, 1 mL to 10 mL 5 mL to 20 mL, 5 mL to 15 mL, or 5 mL to 10 mL of the disclosed liquid medicament/supplement, which may be used for clinical trials and/or for general product presentation to the end user.

WORKING EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric.

I. Comparison Between Exemplary Non-Winterized Standardized Marine Source Oil (Liquid Medicament/Supplement) and Other Currently Marketed Exemplary Fish and Krill Oils Table 1 below depicts a comparison between the chemical components and oxidation amounts between an exemplary non-winterized standardized marine source oil (liquid medicament/supplement) and other exemplary fish and krill oils currently on the market. In Table 1, "Concentrate" refers to Omega 3 wt % concentration>30. Examples of "Concentrate" include Dr. Sear's, concentrated Omega 3 from Nordic Naturals. In Table 1, "Prescription" refers to a standard prescription formulation having an Omega 3 wt % concentration >85% Exemplary "Prescription" fish oil includes Omacore/Lovaza® and Epanova®. In Table 1, "18/12" refers to blended fish oil from herring, sardine, mackerel having a 30 wt % EPA/DHA concentration. In Table 1, "Salmon" refers to fish oil from salmon having a 8 to 16 wt % EPA/DHA concentration. In Table 1, "Krill" refers to oil from krill, typically around 16% concentration in its natural form but varies from 7 to 24 wt % depending on the commercial formulation. In Table 1, "Non-Winterized, Standardized Marine Source Oil" refers to the "Non-Winterized, Standardized Marine Source Oil" of the present invention.

TABLE 1

| | Omega-3 (wt/wt %) | Non-Winterized | DHA:EPA Ratio | Oxydation (totox) | Vitamin $D_3$ (IU) | Vitamin A | CoQ10 |
|---|---|---|---|---|---|---|---|
| Concentrate | >30 | – | Variable for different brands | >5 (10-20) | – | – | – |
| Prescription | >85 | – | Variable for different brands | >5 (10) | – | – | – |
| 18/12 | 30 | – | 2/1 | >5 (10-30) | – | – | – |
| Salmon | 8-16 | – | 1/1 | >5 (10-20) | – | – | – |
| Krill | 7-24 | – | 2/1 | >5 (10-50) | – | – | – |
| Non-Winterized, Standardized Marine Source Oil | 25 | + | 1/1 | <5 | 800/15 ml | 25%/15 ml | 5 mg/15 ml |

As shown in Table 1, "Non-Winterized, Standardized Marine Source Oil" (sourced from Norwegian cod liver) is a non-winterized oil that exhibits considerably less totox, a predetermined 1/1 DHA:EPA ratio, along with predetermined Omega-3, Vitamin $D_3$, and Vitamin A concentrations when compared with currently available over the counter and prescription formulations.

II. Odor and Taste Test Comparison Between Exemplary Non-Winterized Standardized Marine Source Oil and Other Currently Marketed Exemplary Fish Oils Table 2 below depicts an exemplary taste and smell test between fish and krill oils currently on the market and the exemplary non-winterized, standardized marine source oil having the formulation disclosed in Table 1. As evidenced by Table 2, the "concentrate" fish oil, "prescription" fish oil, "18/12" fish oil, salmon oil, and krill oil, exhibited a noticeable, undesirable fishy odor when each sample was smelled and an undesirable, "fishy/fish taste" during the taste test. However, the exemplary non-winterized, standardized marine source oil did not exhibit taste or odor.

TABLE 2

| | Tasteless* | Odorless* |
|---|---|---|
| Concentrate | No | No |
| Prescription | No | No |
| 18/12 | No | No |
| salmon | No | No |
| Krill | No | No |
| Non-Winterized, Standardized Marine Source Oil | Yes | Yes |

*Indicates Without Taste/Odor Masking Agents

The foregoing description provides embodiments of the invention by way of example only. It is envisioned that other embodiments may perform similar functions and/or achieve similar results. Any and all such equivalent embodiments and examples are within the scope of the present invention and are intended to be covered by the appended claims.

What is claimed is:

1. A liquid medicament/supplement composition comprising:
   (a) a non-winterized marine source oil from at least one of fish, krill, squid, or any combination thereof;
   (b) a pharmaceutically acceptable form of vitamin $D_3$ or a derivative thereof admixed in the non-winterized marine source oil;
   (c) a pharmaceutically acceptable form of vitamin A or a derivative thereof admixed in the non-winterized marine source oil;
   (d) optionally a pharmaceutically acceptable form of Coenzyme Q10 or a derivative thereof admixed in the non-winterized marine source oil;

(e) a polyphenol rich vegetable oil at a concentration of less than 25 wt % of total liquid weight of the composition, (f) a concentrated eicosapentaenoic acid, an ethyl ester thereof, a glyceride ester thereof, or a salt thereof; a concentrated docosahexaenoic acid, an ethyl ester thereof, a glyceride ester thereof, or a salt thereof; or mixtures thereof admixed in the non-winterized marine source oil at a concentration of less than 20 wt % of total liquid weight of the composition; and (g) optionally a pharmaceutically acceptable form of melatonin or a derivative thereof admixed in the non-winterized marine source oil, wherein:

the liquid medicament/supplement composition has a totox of less than 5, and the liquid medicament/supplement composition has an overall eicosapentaenoic acid to docosahexaenoic acid ratio (EPA:DHA) calculated as weight % free acids ranging from 2:1 to 1:2 at a concentration ranging from 15 to 35 wt % of total liquid weight of the composition.

2. The liquid medicament/supplement composition of claim 1, wherein the liquid medicinal composition is tasteless, odorless, or a combination thereof.

3. The liquid medicament/supplement composition of claim 1, wherein melatonin or the derivative thereof is present in the liquid medicinal composition.

4. The liquid medicament/supplement composition of any of claim 1, wherein the overall DHA:EPA ratio in the liquid medicinal composition is 1:1.

5. The liquid medicament/supplement composition of claim 1, wherein the liquid medicament/supplement composition is adapted for oral delivery.

6. The liquid medicament/supplement composition of claim 1, wherein the liquid/supplement composition is adapted for skin delivery, rectal delivery, vaginal delivery, or any combination thereof.

7. The liquid medicament/supplement composition of claim 1, wherein the liquid medicament/supplement composition is encapsulated in a capsule for gastro-intestinal delivery.

8. The liquid medicament/supplement composition of claim 1, wherein the non-winterized marine source oil comprises at least cod oil and/or cod liver oil.

9. The liquid medicament/supplement composition of claim 1, wherein the non-winterized marine source oil is Norwegian Cod Liver Oil.

10. A liquid medicament/supplement composition consisting of:

(a) a non-winterized marine source oil from at least one of fish, krill, squid, or any combination thereof;

(b) a pharmaceutically acceptable form of vitamin $D_3$ or a derivative thereof admixed in the non-winterized marine source oil;

(c) a pharmaceutically acceptable form of vitamin A or a derivative thereof admixed in the non-winterized marine source oil;

(d) optionally a pharmaceutically acceptable form of Coenzyme Q10 or a derivative thereof admixed in the non-winterized marine source oil;

(e) a polyphenol rich vegetable oil at a concentration of less than 25 wt % of total liquid weight of the composition;

(f) a concentrated eicosapentaenoic acid, an ethyl ester thereof, a glyceride ester thereof, or a salt thereof; a concentrated docosahexaenoic acid, an ethyl ester thereof, a glyceride ester thereof, or a salt thereof; or mixtures thereof at a concentration of less than 20 wt % of total liquid weight of the composition; and (g) a pharmaceutically acceptable form of melatonin or a derivative thereof admixed in the non-winterized marine source oil, wherein:

the liquid medicament/supplement composition having a totox of less than 5, and the liquid medicament/supplement composition has an overall eicosapentaenoic acid to docosahexaenoic acid ratio (EPA:DHA) calculated as weight % of the free acids ranging from 2:1 to 1:2 at concentration ranging from 15 to 35 wt % of total liquid weight of the composition.

11. A container comprising:

a chamber containing a liquid medicament/supplement composition, and a cap removably, threadly engaged to a top portion of the chamber to seal the chamber, the cap having an inverted nipple such that the internal nipple protrudes into the chamber when the cap threadly engages the top portion of the chamber thereby reducing and/or limiting air within the chamber, wherein:

the liquid medicament/supplement composition contained in the chamber consists of:

(a) a non-winterized marine source oil from at least one of fish, krill, squid, or any combination thereof, (b) a pharmaceutically acceptable form of vitamin $D_3$ or a derivative thereof admixed in the non-winterized marine source oil, (c) a pharmaceutically acceptable form of vitamin A or a derivative thereof admixed in the non-winterized marine source oil, (d) optionally a pharmaceutically acceptable form of Coenzyme Q10 or a derivative thereof admixed in the non-winterized marine source oil, (e) a polyphenol rich vegetable oil at a concentration of less than 25 wt % of total liquid weight of the composition;

(f) a concentrated eicosapentaenoic acid, an ethyl ester thereof, a glyceride ester thereof, or a salt thereof;
a concentrated docosahexaenoic acid, an ethyl ester thereof, a glyceride ester thereof, or a salt thereof; or mixtures thereof, and (g) a pharmaceutically acceptable form of melatonin or a derivative thereof admixed in the non-winterized marine source oil, wherein:

the liquid medicament/supplement composition having a totox of less than 5, and the liquid medicament/supplement composition has an overall eicosapentaenoic acid to docosahexaenoic acid ratio (EPA:DHA) ranging from 2:1 to 1:2 in a concentration ranging from 15 to 35 wt % of total liquid weight calculated as weight % of the corresponding free acids.

12. A method of producing a liquid medicament/supplement composition comprising:

providing a non-winterized marine source oil;

admixing a pharmaceutically acceptable form of vitamin $D_3$ or a derivative thereof in the non-winterized marine source oil;

admixing a pharmaceutically acceptable form of vitamin A or a derivative thereof in the non-winterized marine source oil;

optionally admixing a pharmaceutically acceptable form of Coenzyme Q10 or a derivative thereof thereof in the non-winterized marine source oil;

admixing a polyphenol rich vegetable oil at a concentration of less than 25 wt % of total liquid weight of the composition in the non-winterized marine source oil;

optionally admixing melatonin or a salt thereof in the non-winterized marine source oil; and admixing a concentrated eicosapentaenoic acid, an ethyl ester thereof, a glyceride ester thereof, or a salt thereof; a concentrated docosahexaenoic acid, an ethyl ester thereof, a glyceride ester thereof, or a salt thereof; or mixtures thereof in the non-winterized marine source oil at a concentration of less than 20 wt % of total liquid weight of the composition in order to obtain the liquid medicament/supplement composition;

wherein the obtained liquid medicament/supplement composition has a totox of less than 5, and an overall eicosapentaenoic acid to docosahexaenoic acid ratio (EPA:DHA) calculated as weight % free acids ranging from 2:1 to 1:2 at a concentration ranging from 15 to 35 wt % of total liquid weight of the composition.

* * * * *